United States Patent [19]
Boquet

[11] Patent Number: 5,415,752
[45] Date of Patent: May 16, 1995

[54] PROCESS AND DEVICE FOR THE MANUFACTURE OF A MICROPOROUS MEMBRANE GEL PLATE AND GEL CASSETTE

[75] Inventor: Jean Boquet, Le-Perray-en-Yvelines, France

[73] Assignee: Bertin & Cie, Plaisir, France

[21] Appl. No.: 975,941

[22] PCT Filed: Jul. 8, 1992

[86] PCT No.: PCT/FR92/00650
§ 371 Date: Feb. 23, 1993
§ 102(e) Date: Feb. 23, 1993

[87] PCT Pub. No.: WO93/01491
PCT Pub. Date: Jan. 21, 1993

[30] Foreign Application Priority Data
Jul. 9, 1991 [FR] France .................. 91 08578

[51] Int. Cl.6 ............... G01N 27/26; G01N 27/447
[52] U.S. Cl. .................... 204/182.8; 204/299 R; 204/301; 264/216; 264/217; 425/111
[58] Field of Search ............ 204/299 R, 301, 182.8; 264/216, 217; 425/111

[56] References Cited
U.S. PATENT DOCUMENTS

| | | | |
|---|---|---|---|
| 3,767,560 | 10/1973 | Elevitch | 204/299 R |
| 3,808,118 | 4/1974 | Golias | 204/182.8 |
| 4,381,168 | 4/1983 | Johnson et al. | 414/737 |
| 4,533,307 | 8/1985 | Ansorge | 204/299 R X |
| 4,861,411 | 8/1989 | Tezuka | 156/344 |
| 4,883,597 | 11/1989 | Perlman | 204/182.8 X |
| 4,954,236 | 9/1990 | Kushner et al. | 204/299 R |

FOREIGN PATENT DOCUMENTS

| | | |
|---|---|---|
| 304195 | 2/1989 | European Pat. Off. |
| 309303 | 3/1989 | European Pat. Off. |
| WO87/05230 | 9/1987 | United Kingdom |

Primary Examiner—John Niebling
Assistant Examiner—Jr. Starsiak
Attorney, Agent, or Firm—Bell, Seltzer, Park & Gibson

[57] ABSTRACT

A method and apparatus for fabricating a microporous-membrane for gel plate separating and transferring macromolecules by electrophoresis, the apparatus comprising a peripheral frame (10) provided with a removable bottom plate and including means (54, 58, 60, 64) enabling the membrane to be tensioned after it has been placed on the liquid gel as cast onto the bottom plate.

15 Claims, 4 Drawing Sheets

PROCESS AND DEVICE FOR THE MANUFACTURE OF A MICROPOROUS MEMBRANE GEL PLATE AND GEL CASSETTE

The invention relates to a method and to apparatus for fabricating a plate of gel having a microporous membrane, and intended in particular for separating and transferring macromolecules by electrophoresis.

Such plates of gel (generally agarose or polyacrylamide) have one face covered by an adherent microporous membrane (generally of nitrocellulose or of "nylon"), and must satisfy a certain number of criteria such as gel uniformity, constant gel thickness, absence of bubbles of air between the gel and the membrane, planeness of the membrane, and cleanness of the free face thereof. These plates must also be used shortly after being fabricated since the gel ages poorly (it dries out and cracks quite quickly).

Known methods of fabricating such plates generally consist in placing a membrane by hand on a layer of liquid gel that has been cast onto a support, or in casting the liquid gel onto the membrane that has been placed on the support, and then in allowing the gel to solidify. The results obtained are not very satisfactory with respect to planeness and with respect to cleanness of the membrane, since the liquid gel immediately impregnates the membrane, thereby causing it to lengthen and forming folds or wrinkles, and it may overflow onto the free face of the membrane.

In addition, the above-mentioned known methods are lengthy and fiddly to perform and they do not enable gel plates to be fabricated easily and quickly.

A particular object of the present invention is to avoid those drawbacks of known methods.

An object of the invention is to provide a method and apparatus for fabricating gel plates, enabling the above-mentioned criteria to be satisfied and that are simple and quick in implementation.

Another object of the invention is to provide a method and apparatus for fabricating plates of gel that are of perfect quality and identical to one another.

The invention thus provides a method of fabricating a microporous-membrane gel plate for separating and transferring macromolecules by electrophoresis, the method consisting in casting the gel in liquid form onto a bottom plate carrying a peripheral frame, and being characterized in that it then consists in: placing a dry microporous membrane progressively on the liquid gel; exerting traction on the periphery of the membrane to tension it in substantially uniform manner; and allowing the gel to solidify while keeping the membrane under tension.

Placing the membrane progressively on the layer of liquid gel makes it possible to avoid imprisoning bubbles of air between the gel and the membrane. Uniformly tensioning the membrane placed on the gel makes it possible to ensure that it is plane and serves to accommodate any possible lengthening thereof. By maintaining the membrane under tension, its planeness is conserved during solidification of the gel and subsequently.

Advantageously, the method also consists in giving the membrane an initial shape that has a convex curve towards the gel, in placing the membrane on the gel starting from one end of the plate, and in progressively imparting a plane shape to the membrane as it comes into contact with the gel.

This ensures that the presence of bubbles of air between the gel and the membrane is avoided.

In an implementation of the invention, the method consists initially in fixing the periphery of the membrane on a frame having extensible sides, and then after the membrane has been placed on the liquid gel, in lengthening the sides of said frame to tension the membrane.

Preferably, while the extensible sides of the frame are being lengthened, they are guided along directions that radiate from a fixed point.

The membrane can thus be tensioned in a manner that is substantially uniform in all directions going away from said fixed point, which point is preferably situated on an axis of symmetry of the membrane.

The invention also provides an apparatus for fabricating a microporous-membrane gel plate for separating and transferring macromolecules by electrophoresis, the apparatus comprising a bottom plate carrying a peripheral frame into which the gel is cast in liquid form, and being characterized in that it also comprises: membrane support means at the periphery of the membrane; and tensioning means acting on the periphery of the membrane placed on the gel.

In a preferred embodiment of the invention, the membrane support means comprise a frame having extensible sides to which the periphery of the membrane is fixed, e.g. by spot gluing.

The membrane support frame may have a U-shaped configuration with three extensible sides.

The membrane-tensioning means comprise a thrust mechanism acting on the sides of the extensible frame of the membrane support, and guide means for the extensible sides of said frame.

In a variant, the support frame may be replaced by washers of plastic fixed at regular intervals to the periphery of the membrane, at least along two opposite sides thereof.

The above-mentioned bottom plate is removable and at one end it carries a comb for forming wells at one end of the plate of gel.

Plates of gel fabricated in accordance with the invention are in the form of cassettes that can be handled without difficulty because of the presence of said bottom plate. The bottom plate is made of a plastic that does not adhere to the gel and it is easily removed from the cassette when the cassette is to be used.

In general, the method and the apparatus of the invention greatly simplify the fabrication of gel plates, improving their quality and facilitating their handling.

The invention also provides a gel cassette fabricated in particular by means of said apparatus, characterized in that it comprises a peripheral frame including guide means and support means for a removable bottom plate on which the gel is to be found, and means for tensioning the membrane placed on the gel.

The invention will be better understood and other characteristics, details, and advantages thereof will appear on reading the following description given by way of example and made with reference to the accompanying drawings, in which.

Figure 1:
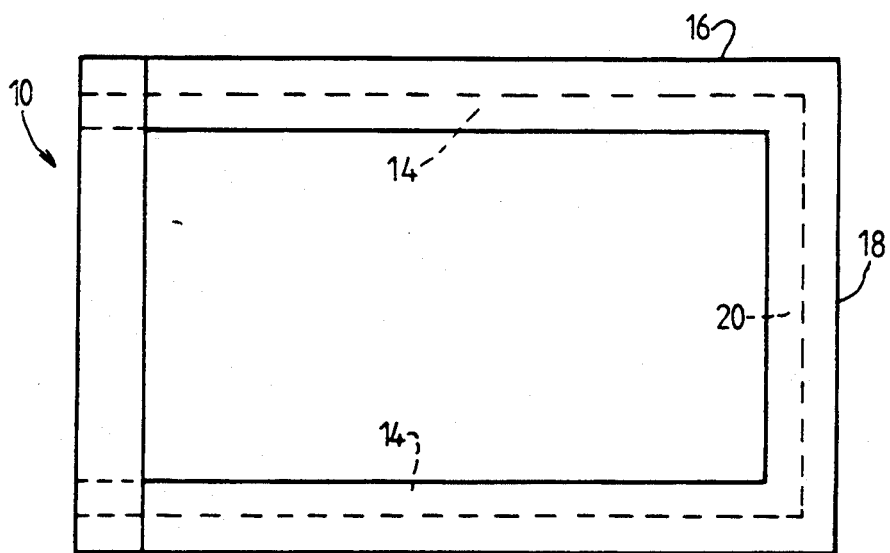
FIG. 1 is a diagrammatic plan view of the frame of a cassette of the invention.
Figure 2:
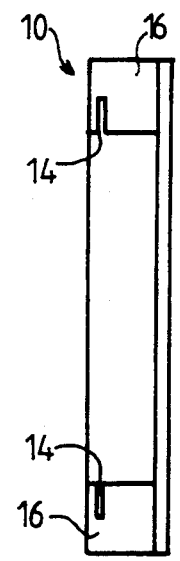
FIG. 2 is an end view of the cassette.
Figure 3:
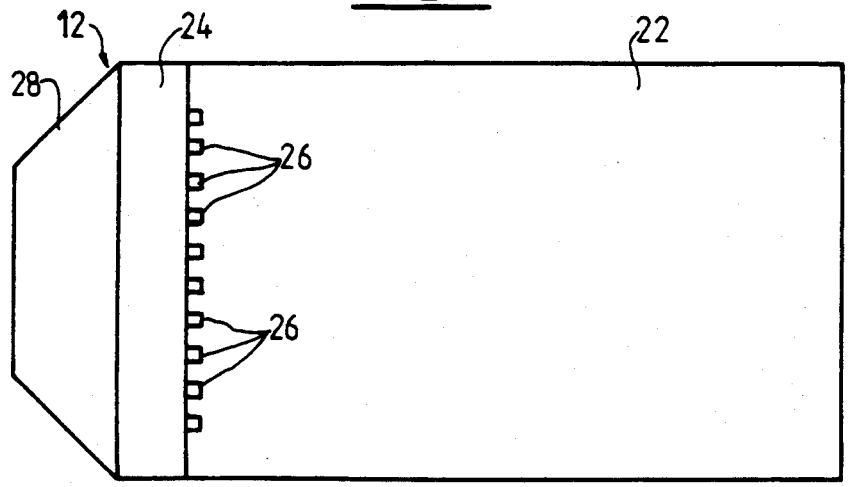
FIG. 3 is a plan view of the bottom plate for said cassette.

A cassette of the invention essentially comprises a frame 10 shown in FIGS. 1 and 2 and a bottom plate 12 shown in FIG. 3. The frame 10 is generally rectangular in shape, and is open at least at one of its ends to receive the bottom plate 12 which is guided like a sliding sheet in grooves 14 formed facing each other in the inside faces of the two long sides 16 of the frame 10, and the transverse side 18 thereof may optionally include a groove 20 interconnecting the grooves 14 in the long sides of the frame.

The bottom plate 12 is essentially constituted by a plane plate 22 that is rectangular in shape and made of a plastic that does not adhere to the gel (e.g. polymethyl-metacrylate) and having one end that includes a comb 24 with parallel teeth 26 for forming wells in the layer of gel cast inside the frame 10. At its comb end, the bottom plate 12 includes an extension 28 enabling it to be handled easily for insertion into the frame 10 or for extraction therefrom.

Figure 4:
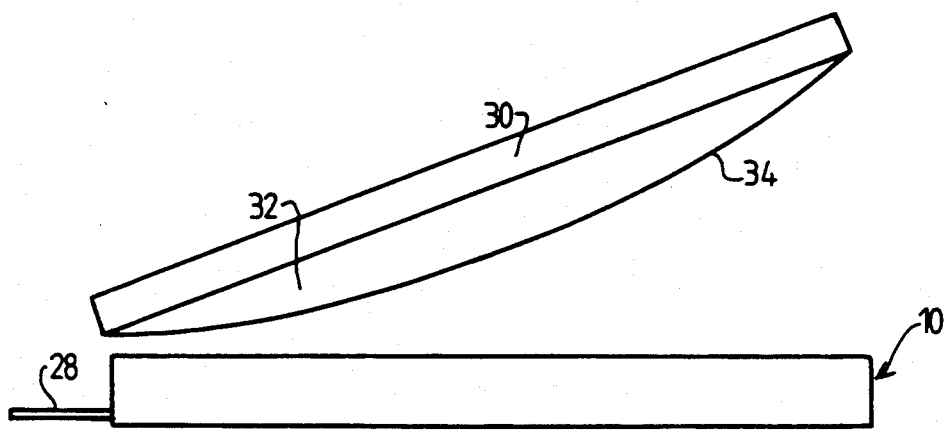
FIG. 4 is a diagram showing the means for curving the membrane.

As shown in part in FIG. 4, the apparatus for fabricating gel cassettes may include a moving part 30 having convex bottom sides 32, e.g. in the form of a sector of a cylinder, for the purpose of supporting a membrane 34 which is to be placed on a layer of liquid gel cast in the frame 10. This moving part 30 is guided to roll relative to the frame 10 from one end to the other thereof so as to deposit the membrane progressively on the layer of gel cast in the frame 10 as the convex curved sides 32 are rolled along the sides of the frame 10.

Any suitable means may be used for temporarily securing the membrane 34 to the part 30.

Figure 5:
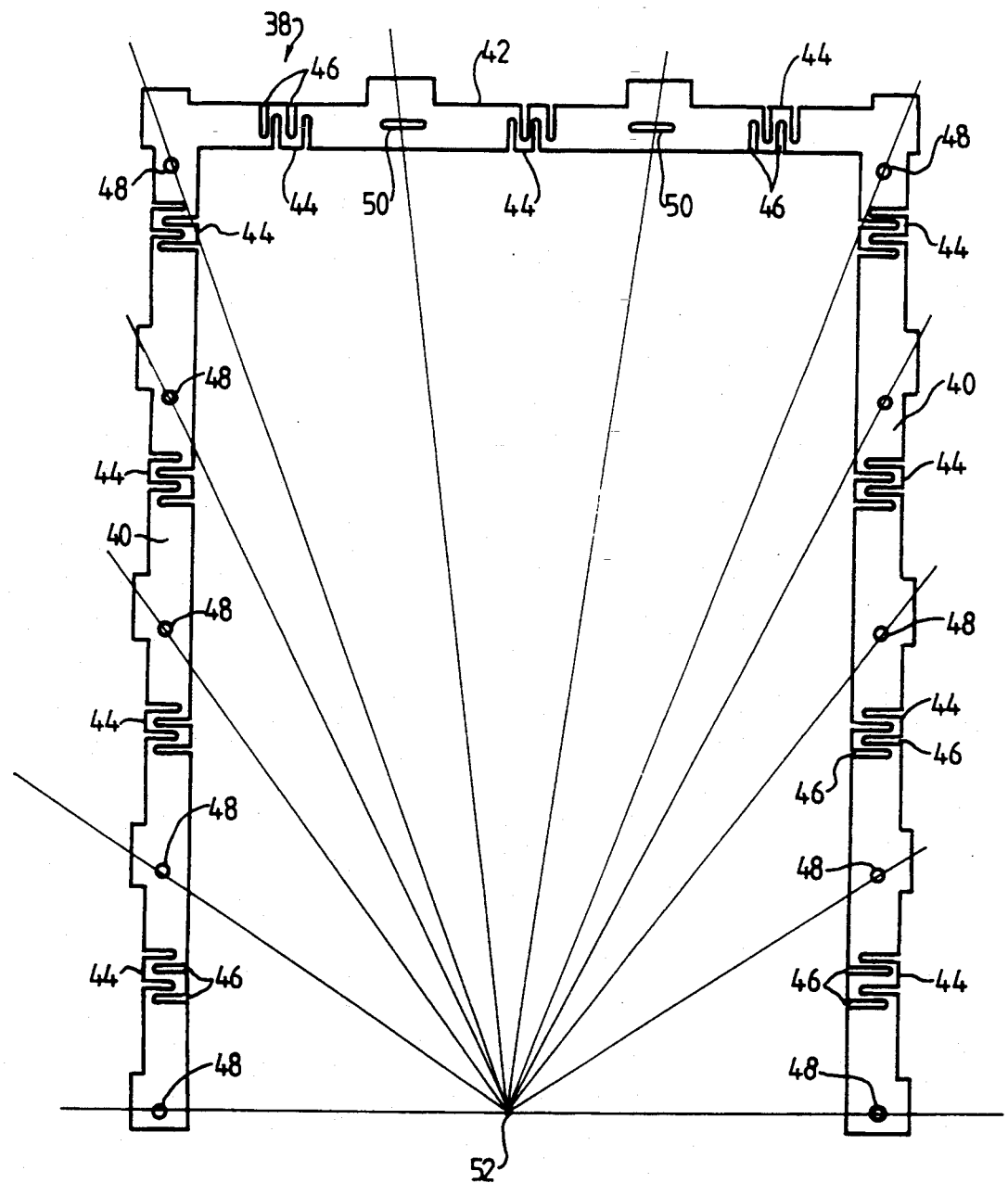
FIG. 5 is a diagrammatic plan view on a larger scale of an extensible membrane-supporting frame.

In addition, the membrane 34 is fixed at its periphery (e.g. by spots of glue or welding) to an extensible frame 38 shown in FIG. 5. The U-shaped frame 38 has two parallel and extensible flat branches 40 that are interconnected at one end by a transverse extensible flat branch 42.

For example, the frame 38 may be injection molded in a relatively rigid plastic, with each of its branches 40, 42 including regularly spaced-apart extensible zones 44 that are obtained by forming transverse slots 46 in the branches of the frame, said slots running from opposite edges, as shown in the drawing.

The non-extensible portions of the branches 40 and 42 of the frame, i.e. the portions in which the zones 44 are not formed, respectively include circular holes 48 and transversely elongate slots 50 for receiving pegs that form part of a tensioning system for the membrane. It will be understood that when the pegs of said system are displaced in outward translation, each in a direction that radiates away from a fixed point 52 to be found in the middle of a line interconnecting the free ends of the parallel branches 40, that are distant from the transverse branch 42, the branches 40 and 42 of the frame 38 will lengthen by longitudinal deformation of the extensible zones 44 and the membrane having its periphery fixed to the frame 38 will be tensioned in all directions away from the point 52.

Figure 6:
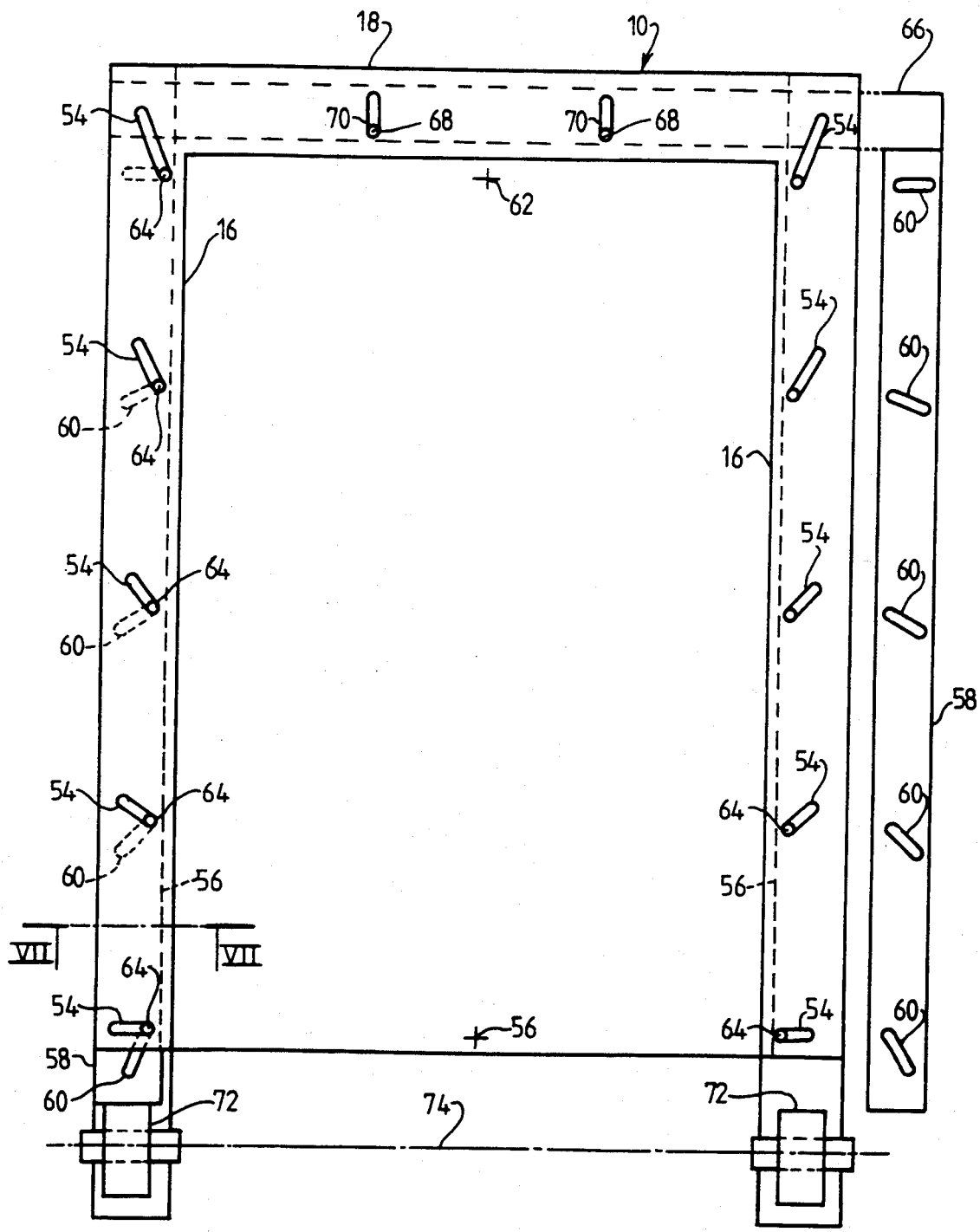
FIG. 6 is a diagram showing the tensioning means.
Figure 7:
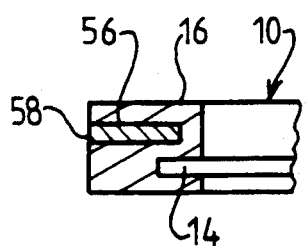
FIG. 7 is a fragmentary section view on line VII—VII of FIG. 6.

FIGS. 6 and 7 show an embodiment of one such tensioning system.

In this embodiment, the top faces of the long sides 16 of the frame 10 in the cassette have elongate slots 54 which extend so as to radiate relative to a fixed point 56, situated in the middle of the line joining together the ends of the sides 16 farthest from the transverse side 18, and corresponding to the point 52 of the extensible frame 38. These slots 54 open out into grooves formed in the longitudinal sides 16 of the frame 10 above the grooves 14 for receiving and guiding the bottom plate 10. Each of these grooves 56 receives a sliding strip 58 which itself includes slots 60 of opposite orientation to the slots 54. In FIG. 6, the right-hand strip 58 is shown outside the frame 10 for reasons of clarity, but it should naturally be understood that it is to be found in the groove 56 of the corresponding side 16 of the frame. When the strips 58 are in place in the grooves 56 in the long sides of the frame 10, their slots 60 radiate relative to a point 62 which is symmetrically disposed relative to the point 56 and which lies in the middle of the line joining together the transverse top slots 60 of the strips 58. Pegs 64 are engaged in the intersections of the slots 54 in the frame 10 and the slots 60 in the strips 58.

The top ends of the strips 58 are interconnected by a transverse strip 66. This transverses strip carries two pegs 68 which are engaged in the longitudinal slots 70 of the side 18 of the frame 10 for the purpose of engaging in the slots 50 in the transverse side 42 of the extensible frame 38.

When the strips 58 are slid upwards along the grooves 56 from the position shown in FIG. 6, the pegs 64 are displaced outwards along the slots 54 of the frame 10, radiating away from the point 56.

Consequently, when the extensible frame 38 on which the membrane is fixed is placed on the top face of the frame 10 so that the holes 48 of the extensible frame engage on the pegs 64, and when the strips 58 are then displaced by sliding along the grooves 56 as mentioned above, the branches 40 and 42 of the extensible frame 38 will lengthen, following the displacement of the pegs 64 along the slots 54 in the frame 10, and the membrane fixed to the frame will be tensioned in substantially uniform manner radiating away from the point 52 which is then superposed relative to the point 56 of the frame 10. For example, when the membrane is about 15 cm×20 cm, the lengthening of the sides of the frame 38 may be of the order of one millimeter in the transverse direction and 2 mm to 3 mm in the longitudinal direction.

The strips 58 are displaced, for example, by cams 72 mounted to rotate about a transverse axis 74 and acting on the free ends of the strips 58. A handle (not shown) enables the cams 72 to be rotated through one-fourth of a turn to displace the strips 58 through about one centimeter.

Figure 8:
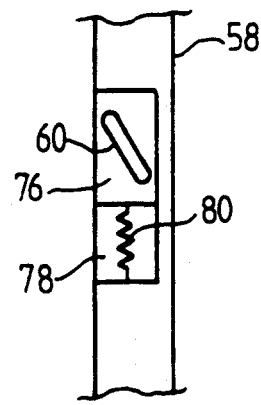
FIG. 8 is a diagram of a portion of a strip in the tensioning means.

To avoid too great a tension on the membrane, the system of FIG. 8 is used: each slot 60 in each strip 58 is formed in a shoe 76 which is slidably mounted in a longitudinal housing 78 in the strip, and a spring or a resilient compression element 80 is disposed between the bottom end of the housing 78 and the shoe 76. Thus translation motion of the strips 58 begins by tensioning the membrane, and then compresses the springs 80, thus automatically limiting the membrane tension to a determined value.

By holding the cams 72 in position, the membrane is kept under tension. It is thus advantageous for the cams and their drive means to be carried by the frame 10 of the cassette. The membrane can then be kept under tension for as long as desired.

Figure 9:
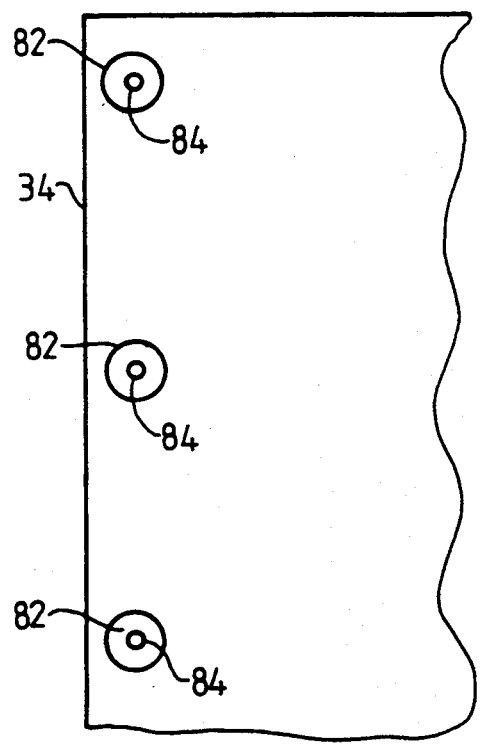
FIG. 9 is a diagram of a variant embodiment of the membrane support.

In the variant embodiment of FIG. 9, the extensible frame 38 is replaced by washers 82 of suitable material fixed at regular intervals to the periphery of the membrane 34, at least along the two long sides thereof, the washers having central orifices 84 that correspond to the holes 48 in the frame 38 for receiving the pegs 64 of the tensioning system.

The apparatus of the invention is very simple to use:

A liquid gel, e.g. agarose at a temperature of about 60° C. to 65° C., is cast in the cassette to form a layer of gel on the bottom plate 12 having a thickness of about 5 mm to 7 mm so as to come flush with the top face of the frame 10. The membrane 34 having either the extensible frame 38 or else the washers 82 fixed to the periphery thereof is placed progressively on the layer of gel starting from one of the ends of the cassette and in such a manner that the holes 48 in the extensible frame 38 or the holes 84 in the washers 82 engage on the pegs 64 of the tensioning mechanism. Once the membrane has been fully deposited on the cassette in this way so as to cover the layer of liquid gel, the handle controlling the cams 72 is rotated through one-fourth of a turn to displace the strips 58 along the grooves in the frame 10, thereby putting the membrane 34 under low tension, and taking up any possible lengthening thereof that may have been caused by it being impregnated by the gel and/or by the temperature of the gel, thus imparting accurate planeness thereto.

The gel is then allowed to solidify by cooling.

Once the gel has solidified, the cassette can be used merely by removing the bottom plate 12 which does not adhere to the gel.

I claim:

1. A method of fabricating a microporous-membrane gel plate for separating and transferring macromolecules by electrophoresis, the method comprising
    casting the gel in liquid form onto a bottom plate carrying a peripheral frame;
    placing a dry microporous membrane progressively on the liquid gel;
    exerting traction on the periphery of the membrane to tension it in substantially uniform manner; and
    allowing the gel to solidify while keeping the membrane under tension.

2. A method according to claim 1, wherein said step of placing a dry microporous membrane progressively on the liquid gel comprises giving the membrane an initial shape that has a convex curve towards the gel, placing the membrane on the gel starting from one end of the plate, and progressively imparting a plane shape to the membrane as it comes into contact with the gel.

3. A method according to claim 1, wherein said step of exerting traction on the periphery of the membrane comprises initially fixing the periphery of the membrane on a frame having extensible sides, and then after the membrane has been placed on the liquid gel, lengthening the sides of said frame to tension the membrane.

4. A method according to claim 3, wherein said step of exerting traction on the periphery of the membrane further comprises guiding the extensible sides of the frame while they are being lengthened along directions that radiate relative to a fixed point.

5. A method according to claim 1, wherein said step of exerting traction on the periphery of the membrane additionally comprises fixing washers on the periphery of the membrane at least along two opposite sides thereof, and then exerting traction on said washers in directions that radiate from a fixed point in order to tension the membrane.

6. A method according to claim 1, comprising a further step performed after allowing the gel to solidify of removing said bottom plate in order to use the plate of gel.

7. Apparatus for fabricating a microporous-membrane gel plate for separating and transferring macromolecules by electrophoresis, the apparatus comprising;
    a bottom plate carrying a peripheral frame into which the gel is cast in liquid form;
    membrane support means at the periphery of the membrane; and
    tensioning means acting on said support means to tension the membrane placed on the gel.

8. Apparatus according to claim 7, wherein the membrane support means comprise a frame having extensible sides to which the periphery of the membrane is fixed.

9. Apparatus according to claim 8, wherein the membrane support frame has a U-shaped configuration with three extensible sides.

10. Apparatus according to claim 7, wherein the membrane support means comprise washers fixed at regular intervals on the periphery of the membrane, at least along two opposite sides thereof.

11. Apparatus according to claim 8, wherein the membrane tensioning means comprise a traction mechanism acting on the membrane support means, and guide means for said support means.

12. Apparatus according to claim 11, wherein said traction mechanism comprises strips guided in translation along grooves in the longitudinal sides of the bottom plate frame, pegs cooperating with the membrane support means and being received in radiating slots formed respectively in the above-mentioned sides of the frame and in the strips, and means for displacing the strips in translation along the grooves in the sides of the frame.

13. Apparatus according to claim 12, including means for automatically limiting the membrane tension to a predetermined value.

14. Apparatus according to claim 7, wherein the bottom plate is removable and carries a comb at one end for forming wells in one end of the cast gel.

15. A gel cassette comprising a microporous membrane a peripheral frame including support and guide means for a removable bottom plate on which the gel is to be cast; and means for tensioning the membrane placed on the gel.

* * * * *